United States Patent [19]

Clement et al.

[11] 4,370,420

[45] * Jan. 25, 1983

[54] PREPARATION OF DRIED BAKER'S YEAST

[75] Inventors: Philippe Clement, Roubaix; Jean-Paul Rossi, Marcq en Baroeul, both of France

[73] Assignee: Societe Industrielle LeSaffre, Paris, France

[*] Notice: The portion of the term of this patent subsequent to May 4, 1999, has been disclaimed.

[21] Appl. No.: 917,726

[22] Filed: Jun. 21, 1978

Related U.S. Application Data

[63] Continuation-in-part of Ser. No. 702,019, Jul. 2, 1976, abandoned.

[30] Foreign Application Priority Data

Jul. 3, 1975 [FR] France .................................. 75 20943

[51] Int. Cl.$^3$ ............................................... C12N 1/18
[52] U.S. Cl. ...................................... 435/256; 426/18; 426/60; 426/62; 435/942
[58] Field of Search ..................... 426/18, 60, 62; 435/256, 245, 942

[56] References Cited

U.S. PATENT DOCUMENTS

| | | | |
|---|---|---|---|
| 1,727,847 | 9/1929 | White | 435/245 |
| 3,120,473 | 2/1964 | DeLottre | 435/256 |
| 3,617,306 | 11/1971 | Pomper et al. | 435/256 |
| 3,885,049 | 5/1975 | Taylor | 426/62 X |
| 3,993,783 | 11/1976 | Langejan et al. | 426/62 X |

FOREIGN PATENT DOCUMENTS 1262648  2/1972  United Kingdom.

OTHER PUBLICATIONS

White, J., Yeast Technology, John Wiley & Sons, Inc., N.Y., 1954, (pp. 53-69).
Gerald et al., Yeast Technology, The Avi Publ. Co., Inc., Westport, Conn., 1973, (pp. 21, 85, 96 & 150).

*Primary Examiner*—David M. Naff

[57] ABSTRACT

Active dried baker's yeast is prepared by selecting a yeast strain stable to drying, cultivating the yeast strain in several aerobic fermentation stages and selecting conditions for the last stage that produce a compressed yeast having preferred gas release characteristics, harvesting and carefully washing the yeast from the last stage to obtain compressed yeast having the preferred gas release characteristics, adding to the compressed yeast an emulsion of an emulsifying agent, dividing the resultant mixture into fine particles, and drying the particles by flash pneumatic conveyor drying and/or fluidized bed drying to obtain active dry yeast having greater than 92% dry matter content. The dry yeast have an activity almost equal to fresh yeast on non-sweetened dough or on sweetened dough.

8 Claims, No Drawings

PREPARATION OF DRIED BAKER'S YEAST

This application is a Continuation-in-Part of application Ser. No. 702,019, filed July 2, 1976, now abandoned.

One aspect of the invention is a process for obtaining a dried yeast, this process comprising the preparation of a fresh yeast capable of being dried without substantial loss of its gassing power.

Another aspect is the active dried yeast thus obtained and the strains used in said process.

The interest in active dried yeasts for bread-making, which are characterised by a dry-matter content equal to or greater than 92%, lies in the fact that their activity lasts for a long time, even at relatively high temperatures. Their disadvantage lies in the fact that drying causes them to loss a fairly large part of the fermenting activity (or gassing power) of the starting fresh yeasts and that, consequently, their activity on an equal dry-matter basis will always be weaker than that of said initial fresh yeasts.

It is fitting to recall here that initially fresh yeasts are generally classified in two categories, those which come from so-called "slow" strains and those which come from so-called "quick" strains. Their distinctive characteristic is their activity upon non-sweetened doughs and upon sweetened doughs (that is to say doughs containing in their composition saccharose or saccharose and glucose).

The first of these have a weak activity upon dough without sugar (saccharose), but they have considerable activity upon sweetened dough, that is to say they are very "osmotolerant". These strains, in general, reach their optimum fermenting activity at low nitrogen and $P_2O_5$ contents (N/D.M.=7 to 7.5 and $P_2O_5$/D.M.=2, with D.M.=dry matter).

The others have a very strong activity upon dough without sugar, but this diminishes rapidly in the presence of increasingly more sweetened doughs; they are not very osmotolerant. These strains, which are generally adapted to maltose fermentation, reach their optimum activity at high nitrogen and $P_2O_5$ contents (N/D.M.=8 to 8.5 and $P_2O_5$/D.M.=2.5 to 3.5).

The optimum composition is the composition for which a larger nitrogen or $P_2O_5$ content gives no more than a slight gain in activity and corresponds specially to a definite deterioration in the stability of the yeast obtained.

Researchers sought essentially drying processes enabling the qualities of fresh yeasts to be better preserved. In fact, the choice of the drying process is not the primary choice. The primary choice is that of the parameters to which the fresh yeast destined for drying must conform in order to be of a nature such as to preserve in the course of the drying, its fermentative activity measured for constant dry matter.

It has been recognized that the fermentative activity on sweet doughs, that is to say doughs containing more than 5% of sugar, is that which is altered most in the course of drying, probably due to the fact that the systems which permit the passage of the sugars through the membrane are the most altered in drying whatever form of drying is used. Consequently, the improvement in the resistance of the yeasts to drying will have the most interesting repercussion in connection with the activity of said dry yeasts on sweet doughs.

Applicants work was to find the main parameters to which a fresh yeast must respond to give rise to minimum loss of activity in its drying and lead to dry yeasts having for equal dry matter, an activity almost equal to the best fresh yeasts on non-sweetened doughs or on sweetened doughs, which is the most difficult case.

The reproducible tests used by the Applicant Company to measure the activity of a yeast are as follows:

Test A

Measurement of the gas released, after mixing with water, using BURROWS' and HARRISON's fermentometer (described in the Journal of the Institute of Brewing, vol. LXV no. 1, January-February 1959),

Test $A_1$ (fresh compressed yeasts)

To 20 g of flour incubated at 30° C., there is added a weight of compressed yeast corresponding to 160 mg of dry matter, this yeast being mixed in 15 ml of water containing 27 g of NaCl per liter and 4 g of $SO_4(NH_4)_2$ per liter; this is kneaded for 40 seconds, using a spatula, so as to obtain a dough which is placed in a water bath set at 30° C.; thirteen minutes after the kneading was begun, the receptacle containing the dough is hermetically closed; the total amount of gas produced is measured after 60, then 120 minutes; this amount is expressed in ml at 30° C. and under 760 mm of Hg,

Test $A'_1$ (dried yeasts)

Similar to Test $A_1$, but prior to kneading, the 160 mg of yeast dry matter are reconstituted or rehydrated in 6 ml of distilled water at 38° C.; this solution is left to stand for 15 minutes; the 9 ml of water complement, mixed with 405 mg of NaCl, is then added, the mixture is poured into 20 g of flour and the final mixture is kneaded for 40 seconds as in Test $A_1$ and the procedure is then continued in the same manner as in Test $A_1$,

Test $A_2$ (fresh compressed yeasts)

Test similar to Test $A_1$, but 100 mg of saccharose are added to the flour; the total amount of gas produced is measured after 60 minutes,

Test $A'_2$ (dried yeasts)

Test identical to Test $A'_1$, but 100 mg of saccharose are added to the flour; the total amount of gas produced is measured after 60 minutes,

Test $A_3$ (fresh compressed yeasts)

Test identical to Test $A_1$, but 2 g of saccharose are added to the flour; the total amount of gas produced is measured after 60 minutes,

Test $A'_3$ (dried yeasts)

Test identical to Test $A'_1$, but 2 g of saccharose are added to the flour; the total amount of gas produced is measured after 60 minutes,

Test $A_4$ (fresh compressed yeasts)

Test identical to Test $A_1$, but 5.5 g of saccharose are added to the flour; the total amount of gas produced is measured after 60 minutes,

Test $A'_4$ (dried yeasts)

Test identical to Test $A'_1$, but 5.5 g of saccharose are added to the flour; the total amount of gas produced is measured after 60 minutes, and the preliminary trials used by the Applicant Company are as follows:

Test B

Measurement of the gas released, with a CHOPIN zymotachygraph, manufactured by M. CHOPIN & Cie, 5 rue Escudier, Boulogne-sur-Seine, France, Test $B_1$ (fresh compressed yeasts and instant dried yeasts not requiring previous reconstitution)

To 250 g of flour there is added a weight of compressed yeast or instant dried yeast corresponding to 1.6 g of yeast dry matter, and 150 ml of salt water (50 g of salt/1.5 l of water); the mixture is kneaded for 6 minutes; the temperature of the dough must be 27° C. at the end of the kneading; the dough is placed in the apparatus and 6 minutes, measured exactly, after the kneading, the thermostatic chamber is put under pressure at 27° C.; the total release of gas recorded on a graph is measured, in ml, after 1 hour and 3 hours, Test $B'_1$ (dried yeasts which have to be reconstituted)

Test identical to Test $B_1$, but prior to the kneading, the dried yeast is reconstituted in distilled water at 38° C. (50 ml) for 15 minutes; the water and salt complement is added to the product of the 15 minutes' reconstitution, Test $B_2$ (fresh compressed yeasts and instant dried yeasts)

Test identical to Test $B_1$, but there are added to the flour 5% of sugar, 5% of margarine and 4.0 g of yeast dry-matter; after kneading, 250 g of dough are taken and introduced into the apparatus; the total amount of gas released is measured after 1 hour and 1 hour 30 minutes, Test $B'_2$ (non-instant dried yeasts)

Test identical to Test $B_2$, but, prior to kneading, the dried yeast is reconstituted in 50 ml of distilled water at 38° C. for 15 minutes; the water and salt complement is added to the product of the 15 minutes reconstitution.

The process according to the invention, for preparing the above-mentioned dried yeasts, having a dry-matter content greater than 92%, preferably between 94 and 97%, is characterised by the fact that there is subjected to careful drying—that is to say to particularly gentle drying—a fresh, compressed yeast, containing 30–35% of dry matter, to which has been added an emulsion of an emulsifying agent having an HLB (Hydrophilic-Lipophilic-Balance) value between 3 and 11 in water, obtained by cultivating strains of yeast which are stable to drying, the cultivation conditions being such that the amount of buds on the yeast obtained is less than 5% and, preferably, less than 1% of the total number of yeast cells, the amount of proteins in the yeast obtained corresponds to the optimum activity of the cultivated strains, and, in addition, the composition of the fresh compressed yeast satisfies the following inequalities:

$$\frac{trehalose}{dry\ matter} \geq 12\%$$

$$2.3 \leq \frac{nitrogen}{P_2O_5} \leq 3.8$$

cryoscopic lowering of the water outside the yeast is below 0.5° C.

It is pointed out that, in order to measure the cryoscopic lowering of the water outside a compressed yeast containing 30–35% of dry matter, a cream is made with 100 g of the compressed yeast and 30 g of demineralised water, this cream is centrifuged and the cryoscopic lowering of the supernatant liquid obtained is measured, for example using a cryoscope of the BECKMAN type (PROLABO no. 0329 600). The lowering of the freezing point measured is proportional to the amount of gram molecules of substances dissolved in the water outside.

It was found that yeast particularly valuable for sweetened doughs were obtained when the strain used within the scope of the above-mentioned process was a distillers' yeast which was slow, very osmotolerant and stable to drying, such as that which was deposited at the N.C.Y.C. (National Collection of Yeast Cultures, Agricultural Research Council's Food Institute, Colney Land, Norwich, Norfolk NR4 7UA, England, under number R 30, or one of the hybrids which were obtained by crossbreeding and successive selection, carried out with the aim of obtaining strains which are both quick and osmotolerant, and which are deposited at the N.C.Y.C. under numbers R 37 and R 38.

The invention also aims at providing the above-mentioned strain and hybrids as new industrial products.

The three strains R 30, R 37 and R 38 are of the species Saccharomyces Cerevisiae. In the standard taxonomic tests carried out by the N.C.Y.C., according to the work by J. LODDER, The Yeasts, A Taxonomic Study, 1970, they are distinguished essentially by the following characteristics, assembled in table I.

TABLE I

| Tests | R 30 | R 37 | R 38 |
|---|---|---|---|
| Assimilation of the sugars | | | |
| Trehalose | + | + | — |
| Melezitose | + | + slight latent | — |
| α-methylglucoside | + | + latent | — |
| Fermentation of the sugars | | | |
| Galactose | + 3 weeks | + 24 hours | + 2 weeks |
| Increase in medium without vitamins | — | — | ∓ |
| Sporulation on potassium acetate | 1 to 2 spores per ascus | 3 spores per ascus | 2 to 3 spores per ascus |

For the point of view of the biochemistry of the yeasts, these three strains are distinguished very little from one another, especially the isolated strain of yeast R 30 and the yeast hybrid R 37, but the technological characteristics of these two strains are very different. The taxonomic tests are of little value to distinguish the strains within the same species, all the more so since their reproducibility is uncertain. It is because of their very weak reproducibility that no test giving a description of the morphology of the yeasts is given.

Apart from the above-mentioned characteristics, the invention aims further at other characteristics which are made use of, preferably, at the same time and which will be mentioned more explicitly hereinafter.

And it can, in any case, be well understood using the rest of the description, which follows, and the accompanying examples, the said additional description and examples being given in keeping with preferred methods of carrying out the invention.

To manufacture a dried yeast whose activity is comparable to the activity of the best available fresh compressed yeast, the same quantities of dry matter being taken into consideration, the procedure may be as follows or in an equivalent manner.

Firstly there is selected, according to the invention, a yeast strain stable to drying and capable of giving a fresh yeast having either a release of gas of more than 45 ml in Test $A_3$, or a release of gas of more than 105 ml in Test $A_1$ (for the whole of the 2 hours), and satisfying preferably to both characteristics.

The strain is then cultivated as usual in several aerobic fermentation stages with continuous introduction of the foods for the yeasts and of the principal ingredients (molasses, source of nitrogen, source of $P_2O_5$).

The last aerobic fermentation stage leading to the harvesting of the yeast which is be dried is conducted so as to lead to a compressed yeast responding to the above-indicated parameters.

To do that:

Introduction of nitrogen and of $P_2O_5$ are calculated so as to lead to the values selected, and the optimum nitrogen content is determined by successive tests around the values which are generally used for the type of strain cultivated;

at the end of this last stage, during the final hours, the flows of foods and ingredients (molasses, nitrogen, $P_2O_5$) are sufficiently reduced to obtain the desired trehalose and budding ratio.

Generally, it is advantageous for the dilution of the culture medium, during this last stage, to be as low as possible. This dilution can be characterised by the following ratio:

$$\frac{\text{weight of the culture medium in the vat at the end of multiplication}}{\text{molasses poured into the vat during the last multiplication cycle}}$$

which must be comprised between 3.5 and 7 and, preferably, between 3.8 and 5.

Also in general, during all of the multiplication cycles, care must be taken to introduce all the growth factors known as indispensable to the yeast, such as magnesium, biotine, and the group B vitamins.

The yeast harvested at the end of the last aerobic fermentation stage, called "last multiplication cycle", is carefully washed to obtain the desired cryoscopic lowering of the external water of the fresh yeast.

As mentioned above, the cryoscopic lowering of the water outside the yeast is proportional to the gram-molecules of dissolved substances. These dissolved substances can have action which is really disastrous during drying.

It has been made evident that if the yeast contained a content of 0.5 g of NaCl per 100 g of yeast dry-matter resulting either from an acid treatment or from the use of the salt process to filter the yeast, as described in British Pat. No. 763,926, there is recorded with drying a loss of additional strength of 5% with regard to dough without sugar and of 8% with regard to sweetened dough.

Having thus obtained—either starting from one of the three N.C.Y.C. strains Nos. R 30, R 37 and R 38, or starting from any other strain stable to drying and satisfying the abovementioned selection criteria—a fresh yeast which has the lowest possible amount of budding and which satisfies the four following conditions regarding its composition:

amount of proteins corresponding to the optimum activity, trehalose content with respect to dry matter $\geq 12\%$ $$2.3 \leq \frac{\text{nitrogen content}}{P_2O_5 \text{ content}} \leq 3.8$$

cryoscopic lowering of the water outside the fresh yeast to 30–35% of dry matter below 0.5° C., this fresh yeast is subjected to a particularly careful drying.

Flash (pneumatic conveyor) drying, fluidised bed drying or a combination of these two methods of drying can be used.

This drying treatment is performed in the presence of emulsifying the stabilising agents having film-forming properties suitable for protecting the yeast during drying and for facilitating its reconstitution.

Thus, there can be added to the yeast an emulsion in water of one of the following emulsifiers: sorbitol ester, lactic ester, diacetyl tartaric ester of mono- and diglycerides, stearoyl-2-lactylate of sodium or calcium and one of the following stabilizers: gum arabic, guar gum or carraghenate.

The content of emulsifying agents is calculated so as to represent 0.5 to 2% of the finished product, and that of the agent stabilising the emulsion 0.5% to 1% of the finished product.

Before the first drying phase, the fresh yeast, the dry-matter content of which is generally from 30 to 35%, is finely divided by extrusion through a grid having a mesh width of between 0.5 and 3 mm.

Pneumatic conveyor drying is of interest to permit particularly brief drying.

The yeast is dried to at least 92% of dry matter, preferably to 94 to 97% of dry matter. The dry matter of the yeast obtained is controlled by blowing into the final compartment of the drying apparatus used, dehydrated air having a relative humidity which is in equilibrium with the dry matter desired for the yeast.

In order to prevent any beginning of oxidation of the yeast, which is harmful to its preservation, all the drying, or the final stages of drying, when for example the yeast has reached a dry matter content of 80%, can be carried out under vacuum or under inert gas such as, for example, nitrogen or carbon dioxide.

All the drying is preferably carried out continuously and is conducted in such a manner that the temperature of the yeast never reaches 35° C. Although that is not of prime importance, it is preferable for the total period of drying to be as short as possible. It should be less than 5 hours, and it will preferably be equal to or less than 1 hour.

The dried yeasts thus obtained can be incorporated in the dough either after reconstitution at 38° C., or immediately. Similar results are obtained for these dried yeasts in tests B and B'.

They are preferably conditioned under vacuum or under an inert atmosphere, in such a manner that the residual oxygen content is less than 2% of the volume of the conditioning restored to atmospheric pressure.

This being so, the invention is illustrated by the following examples.

EXAMPLE 1

Selection of the strains

For each strain to be tested, a 24-hour culture is made, with recourse to 3-liter fermentors (see Yeast Technology, J. WHITE, 1954-pages 103 to 106). The culture medium has a total volume of 1100 ml. The sugar is introduced in the form of molasses. The air is filtered on a sterile membrane of trademark "Millipore" at the rate of 1 m³/hour for a battery of three fermentors. Innoculation is carried out with 300 mg of yeast obtained by anaerobic culture in flasks.

The strains R 30, R 37 and R 38 were thus preselected. In Table II there are recorded the results obtained during a series of tests made with these three strains and with hybrids (tests in parallel recorded on the last line) of quick yeast adapted to maltose and stable to drying.

TABLE II

| | Results | | |
|---|---|---|---|
| Strains tested | Test $A_1$ 1 hour (ml) | Test $A_3$ 1 hour (ml) | Invertase activity (invertase units) |
| Distillers' yeast N.C.Y.C. R 30 | 25 | 58 | 30 |
| Yeast hybrid N.C.Y.C. R 37 | 35 | 58 | 60 |
| Yeast hybrid N.C.Y.C. R 38 | 33 | 66 | 70 |
| Hybrids of quick yeast adapted to maltose | 60 | 45–57 | 50–200 |

The yeasts harvested are very unstable. The results obtained do not correspond exactly to what can be obtained within the scope of the production of yeasts stable to drying, or of compressed commercial yeasts. They cannot be reproduced very exactly. The results obtained must always be evaluated with reference to one or two control strains.

EXAMPLE 2

Recourse is had to a battery of pilot fermentors constituted as follows:
- internal diameter 45 cm, height 85 cm, useful volume 80 l,
- double casing permitting regulation of the temperature of the fermenting wort,
- air inlet situated at the base of the vat, surmounted by an agitator rotating at 150 r.p.m. driven by a 3 HP motor,
- device for flow of the ingredients through distributing pumps of BRANN and LUBBE brand, having an hourly output which can be regulated between 0.1 liter/hour and 6 liters/hour,
- device for automatic regulation of the pH to a value as shown recorded, by inflow of dilute sulphuric acid, and
- device for regulating the height in the vat of the fermenting liquid by inflow of anti-foam agent.

In each test, the yeast is inoculated at hour 0 into the base of a 35-liters vat containing 160 g of molasses, 15 g of nitrogen and 15 g of $P_2O_5$. The fermentation test lasts 14 hours, at the end of which the yeast produced is harvested.

At the end of 14 hours, the weight of the vat is 63 kg (a little more than 60 liters) and the amount of molasses poured in is 13.1 kg containing 50% of Clerget sugar method. The dilution of these tests is thus:

$$\frac{\text{weight of yeasted wort in the vat at the end of fermentation}}{\text{weight of molasses poured in the vat}} = \frac{63}{13.1} = 4.8$$

The molasses are poured in continuously, in increasing amounts at each hour, except during the final hours. Nitrogen is introduced in the form of ammonia in solution; it is also caused to flow in increasing amounts at each hour ("exponential" curve), this inflow being stopped at hour 12. Phosphorus is introduced in the form of phosphoric acid for 5 hours. The amounts of nitrogen and $P_2O_5$ introduced are calculated so as to obtain the desired composition taking as hypothesis a yield:

$$\frac{\text{yeast containing 30\% of dry matter}}{\text{molasses containing 50\% of Clerget sugar}} = 100$$

and an assimilation yield of $P_2O_5$ and mineral nitrogen plus nitrogen assimilable brought by the molasses, of 100.

The amount of air blown in is regulated as a function of the amount of alcohol in the vat.

The yeast is separated off and washed in a centrifuge, dehydrated to 32–33% of dry matter on a rotating filter under vacuum, employing the salt process (salt which is eliminated very carefully by inclined sprinklers on the rotating filter) and finally extruded either in 500 g blocks or in strands 0.6 mm in diameter.

Washing is carried out in such a manner that the cryoscopic lowering of the supernatant liquid obtained starting from a "cream" constituted by 100 g of yeast containing 30–35% of dry matter taken at the coming out of the filter and 30 g of demineralised water, is of 0.3° C.

To the yeast intended for drying, there is added a thin emulsion, constituted by sorbitol ester and gum arabic, at the rate, respectively, of 1.5% and 0.7% of the yeast dry-matter.

The yeast extruded into strands 0.6 mm in diameter is dried on a laboratory discontinuous fluidiser in 30 to 40 minutes, so that the temperature of the yeast does not exceed 35° C. during a drying.

Great attention is paid to the fluidisation and to the beginning of the drying which must be quick and homogeneous. In order to do this, the yeast is vibrated manually at the beginning of drying.

At the end of the drying, dehydrated air containing 5 g of water per kg of air is blown in so that the yeast can be regulated to the desired dry matter.

The yeast obtained contains 94% of dry matter; it is presented in the form of small strands, 1 to 2 mm long, light cream in colour.

This treatment enables the results obtained in fermentors of 3 liters total volume (culture medium 1.1 l) to be confirmed, and the stability to drying of the preselected strains to be tested.

This treatment is applied to the three strains deposited at the N.C.Y.C. under numbers R 30, R 37 and R 38, and to a hybrid of quick yeast, adapted to maltose and particularly stable to drying.

The inflow of nitrogen is calculated to obtain a yeast containing 7% of nitrogen with respect to dry matter with the N.C.Y.C. strain R 30, and 8% of nitrogen with respect to dry matter with the three other strains.

The inflow of $P_2O_5$ is calculated to have a nitrogen/$P_2O_5$ ratio of 3.2.

The yields: $\frac{\text{yeast containing 30\% of D.M.}}{\text{molasses containing 50\% of Clerget sugar}}$ obtained for these four strains are between 95 and 100, without the differences obtained being significant. Consequently, the composition objectives aimed at are achieved.

The trehalose content with respect to yeast dry matter is above 13% and the cryoscopic lowering of the water outside the yeasts after passing over a rotating filter is below 0.3° C. The amount of budding of the yeasts obtained is 1%.

The results obtained for the yeasts containing 32–33% of dry matter and 94% of dry matter are recorded in the recapitulatory table III (lines 1 to 4).

EXAMPLE 3

In order to show by comparison that the above-defined parameters are indispensable to obtain compressed yeasts resistant to drying, commercial fresh compressed yeasts obtained immediately after leaving the facility were dried, i.e.:

an extremely fast fresh yeast marketed in Great-Britain a fast fresh yeast marketed in France.

The drying was conducted according to the procedure defined in example 2. The results obtained are reported in Table III.

EXAMPLE 4

In the recapitulatory Table III (line 7) there appear the best results recorded with a dried yeast prepared from a North American slow strain obtained in commerce.

Measurement, with a CHOPIN zymotachygraph, of the gas released from by the dried yeast obtained with a slow strain, manufactured in North America, was carried out using test B' (B'$_1$ and B'$_2$); in fact, unlike all the other yeasts tested, this dried yeast, of American origin, gives results which are clearly inferior by directly incorporating the yeast into the dough.

TABLE III

| | FRESH COMPRESSED YEAST | | | | | | | | DRIED YEAST | | | | | | | |
|---|---|---|---|---|---|---|---|---|---|---|---|---|---|---|---|---|
| | | | | | Test $B_1$ | | Test $B_2$ | | | | | | Test $B_1$ | | Test $B_2$ | |
| | $A_1$ | $A_2$ | $A_3$ | $A_4$ | 1 h | 3 h | 1 h | 1 h 30 | $A'_1$ | $A'_2$ | $A'_3$ | $A'_4$ | 1 h | 3 h | 1 h | 1 h 30 |
| Distillers' yeast N.C.Y.C. No. R 30 (example 2) | 37 + 48 = 85 | 52 | 56 | 40 | 260 | 1 200 | 520 | 900 | 32 + 43 = 75 | 45 | 47 | 32 | 230 | 1 050 | 430 | 750 |
| Yeast hybrid N.C.Y.C. No. R 37 (example 2) | 45 + 66 = 111 | 55 | 56 | 24 | 310 | 1 480 | 520 | 900 | 40 + 58 = 98 | 48 | 48 | 20 | 270 | 1 300 | 430 | 750 |
| Yeast hybrid N.C.Y.C. No. R 38 (example 2) | 45 + 64 = 109 | 54 | 58 | 24 | 300 | 1 460 | 540 | 950 | 40 + 57 = 97 | 47 | 49 | 20 | 260 | 1 300 | 450 | 790 |
| Hybrid of quick yeast adapted to maltose and stable to drying (example 2) | 55 + 80 = 135 | 59 | 49 | 22 | 350 | 1 700 | 450 | 800 | 48 + 70 = 118 | 50 | 41 | 18 | 300 | 1 500 | 380 | 680 |
| Fresh compressed yeast just issuing from the facility in the United Kingdom (example 3) | 79 + 103 = 182 | 84 | 64 | 11 | | | | | 24 + 48 = 72 | 26 | 16 | 4 | | | | |
| Fresh compressed yeast just issuing from the facility in France (example 3) | 56 + 81 = 137 | 60 | 50 | 24 | | | | | 38 + 57 = 95 | 41 | 32 | 14 | | | | |
| Dried yeast obtained with a slow strain from North America (example 4) | | | | | | | | | 34 + 38 = 72 | 42 | 32 | 14 | 200 | 930 | 240 | 450 |

On examining this Table III, it appears that the dry yeasts obtained from compressed fresh yeasts which have been prepared in accordance with the invention preserve an activity which is comparable with that of said fresh yeast before drying; on the contrary, it appears clearly that the results recorded with the dry yeasts dried under the same conditions as above but using a commercial compressed fresh yeast taken as delivered from the facility are not at all comparable with the results recorded for these fresh yeasts before drying.

We claim:

1. A process for preparing a yeast composition in solid particular form, consisting essentially of an active baker's yeast and an emulsifying agent, said process comprising successively
    (1) selecting a yeast strain stable to drying, and which has the further characteristic in fresh compressed yeast form of releasing at least 105 ml of gas in test $A_1$, in two hours
       wherein, in said test $A_1$, the said fresh baker's yeast in an amount corresponding to 160 mg of dry material, and diluted in 15 ml of water containing 27 g of NaCl and 4 g of $(NH_4)_2SO_4$ per liter, is added to 20 g of flour incubated at 30° C. and kneaded for 40 seconds to obtain a dough, maintaining said dough at 30° C. in a vessel for 13 minutes after the beginning of said kneading, thereafter hermetically sealing said vessel and measuring the total amount of gas produced, in ml at 30° C. and 760 mm of Hg, after the expiration of 120 minutes;
    (2) cultivating said yeast strain discontinuously in a plurality of multiplication cycles, having several hours duration each, and carried out in vats previously provided with inoculating yeast and water, by regulated inflows of molasses and other nutrients including nitrogen and $P_2O_5$, harvesting the yeast the end of each multiplication cycle, and wherein during the last of said multiplication cycles, the cultivation conditions consisting essentially in the combination of:
       (i) continuous inflows of the molasses;
       (ii) maintaining a value of between about 3.8 and about 5 for the weight ratio of $$\frac{\text{(Culture medium)}}{\text{(molasses)}}$$

wherein the term "(culture medium)" refers to the entire content of the culture vat including water, yeast and nutrient substances at the end of the last multiplication cycle, and
          wherein the term "(molasses)" refers to the total quantity of molasses introduced into the vat during said last multiplication cycle,
       (iii) regulating the respective inflows of molasses nitrogen and $P_2O_5$ such that the yeast harvested at the end of the last multiplication cycle has
       (A) an amount of buds which is less than 5%, and
       (B) a protein content in said yeast in an amount which corresponds to the optimum activity of the selected strain, wherein the said optimum activity is the activity which corresponds to the protein content of the yeast for which a higher protein content gives no more than a slight gain in activity and will cause a definite deterioration in the stability of the yeast, and
       (C) the following characteristics
          (a) a trehalose content in the dry matter of at least 12%
          (b) a ratio of nitrogen to $P_2O_5$ content of between 2.3 and 3.8; and
       harvesting the thus-cultivated yeast at the end of said last multiplication cycle,
    (3) thereafter separating, washing and filtering or compressing the thus-cultivated and harvested yeast so as to obtain a compressed yeast having the characteristic that the supernatant liquid obtained by centrifuging a cream formed of 100 g of said compressed yeast containing 30–35% of dry matter, and admixing the same with 30 g of demineralized water will exhibit a cryoscopic lowering of at most 0.3° C.;
    (4) then adding to said thus-obtained compressed yeast an emulsion of an emulsifying agent having an HLB value of between 3 and 11 in water and having film forming properties sufficient to provide adequate protection and to facilitate its reconstitution in use, and said emulsifying agent being between about 0.5 and 2% by weight of the finished dry yeast product; and
    (5) finally, dividing into fine particles the thus-obtained compressed yeast emulsifying agent composition and drying the same in particulated condition under gentle drying conditions, either by flash pneumatic conveyor drying, or fluidized bed drying, or a combination of flash pneumatic conveyor drying and fluidized bed drying, and at least sufficient to reduce the water content thereof to the level of a dry matter content between 94% and 97%.

2. The process of claim 1 wherein the amount of buds in said step (2)(iii) A is less than 1%.

3. The process according to claim 1, wherein the drying process in said step (5) is carried in several stages, the final stage being carried out under an inert gas of nitrogen or carbon dioxide.

4. The process according to claim 1, wherein the drying process in said step (5) is further conducted under vacuum when the yeast being dried has reached a dry matter content of about 80%.

5. An active dry baker's yeast composition prepared according to the process of claim 1.

6. An active dry baker's yeast composition prepared according to the process of claim 2.

7. An active dry baker's yeast composition prepared according to the process of claim 3.

8. An active dry baker's yeast composition prepared according to the process of claim 4.

* * * * *